United States Patent [19]

Tapper

[11] Patent Number: 4,822,334
[45] Date of Patent: Apr. 18, 1989

[54] ELECTRICAL DOSIMETRY CONTROL SYSTEM

[76] Inventor: Robert Tapper, 1935 Armacost Ave., Los Angeles, Calif. 90025

[21] Appl. No.: 937,910

[22] Filed: Dec. 4, 1986

[51] Int. Cl.$^4$ .............................................. A61N 1/40
[52] U.S. Cl. .................................. 604/20; 128/419 R
[58] Field of Search ...................... 128/303, 13, 419 R, 128/419 F, 783; 604/20

[56] References Cited

U.S. PATENT DOCUMENTS

| | | | |
|---|---|---|---|
| 4,141,359 | 2/1979 | Jacobsen et al. | 128/419 R X |
| 4,509,520 | 4/1985 | Dugot | 128/419 F |
| 4,548,208 | 10/1985 | Niemi | 128/419 R X |
| 4,574,809 | 3/1986 | Talish et al. | 128/419 F |
| 4,619,252 | 10/1986 | Ibott | 604/20 X |
| 4,622,031 | 11/1986 | Sibalis | 604/20 |

FOREIGN PATENT DOCUMENTS 147524 7/1985 European Pat. Off. .............. 604/20

Primary Examiner—Edward M. Coven
Attorney, Agent, or Firm—Fulwider, Patton, Rieber, Lee & Utecht

[57] ABSTRACT

A method and apparatus for electrical dosimetry control in the application of electric currents to the human body, dosage being determined by the product of time and electrical current, wherein electrical current magnitude and/or time may be selectively varied by the patient or therapist during an administration procedure, for the comfort or convenience of the patient, without altering the total predetermined dosage to be administered, the system typically including means for setting the desired total dosage to be administered, means for selectively varying the magnitude of electrical current applied to the patient, means for integrating the applied current over time to obtain an electrical current-time product providing a running measure of dosage during the administration procedure, means for comparing the running measure with the total dosage desired, and means for terminating the administration procedure once the desired total dosage has been delivered to the patient.

5 Claims, 2 Drawing Sheets

ELECTRICAL DOSIMETRY CONTROL SYSTEM

BACKGROUND OF THE INVENTION

This invention relates generally to improvements in methods and apparatus for controlling dosimetry in the application of electric currents to a load and, more particularly, to a new and improved electrical dosimetry control system useful in the application of electric currents to a human body or the like, dosage being determined by the product of time and electrical current, wherein electrical current magnitude and/or time may be selectively varied by the patient or therapist during an administration procedure, to suit the comfort or convenience of the patient, without altering the total predetermined dosage to be administered. While the invention may be applied to dosimetry control in the application of electrical currents to any suitable load, it is particularly applicable to iontophoretic systems used for galvanic therapy and/or to infuse precise amounts of medication in applying electrical currents to the human body.

Around the turn of the century the art disclosed a plethora of electrode types for applying "electric treatments" to the human body. The electrodes were normally placed upon the body in relation to the position of an organ to be treated.

These "electric treatments" encompassed a wide range of applications. For example, galvanic (direct current) treatments have been popular in the past for their polar effects on ionized molecules, causing the ionized molecules to be driven through the skin, usually superficially. This phenomenon is known as iontophoresis or ion transfer, and it has been employed for the introduction of medicants, or even simply moisture, into the skin of a patient.

More specifically, some ions of zinc and copper can be employed in the treatment of some skin infections, and chlorine ions have been employed for the loosening of superficial scars. Further, vasodilating drugs can be used in rheumatic and peripheral vascular affections, and skin anesthesia can be produced by iontophoresis of local anesthetic drugs. It has been suggested that application of direct current to carefully selected areas of a living animal can produce anesthetic effects.

Although the above mentioned iontophoretic treatments have been found to be effective, some patients experience considerable discomfort when sufficiently high levels of electrical current are applied, and patient tolerance can vary widely. Previously, not much could be done to relieve patient discomfort other than to stop and start treatments until the necessary dose is ultimately applied. Of course, such procedures result not only in patient discomfort, but also in eratic and inaccurate dosimetry.

The aforementioned undesirable effects of iontophoretic treatment have resulted in a less than enthusiastic reception of iontophoretic techniques by the medical community in spite of the great and varied advantages to be realized through their use and development.

More specifically, in the application of electrical currents to the human body for therapeutic benefits, two variables affect the outcome of the treatment, i.e., the quantity of electrical current administered and the length of time the current is administered. Since each of these two variables act to offset each other during treatment, it has been an age old desire on the part of the practitioner to have some means of accurately measuring and controlling the composite or product of these two components as an indication of administered dosage. Furthermore, the result of this interaction of two distinct dosage determining variables must be consistently repeatable for reliable dosimetry.

Present technology measures time and current as two separate variable parameters and relies on the practitioner to interpolate the results with often great inaccuracy and little likelihood of replicating the treatment with precision. The present means of accomplishing this is to rely on an ammeter for electrical current readings and a suitable timing mechanism to indicate the duration of treatment. The variability comes about because, as previously indicated, no two patients have the same tolerance for electrical current and the practitioner is forced to vary the current according to patient tolerance. Moveover, patient tolerance can also vary considerably throughout treatment, necessitating continuous changes in electrical current levels. Keeping track of administered dosage, in the face of such complex variabilities, is a virtually impossible task.

Hence, those concerned with development and use of iontophoretic devices and the like in the medical field have long recognized the need for improved electrical dosimetry measurement and control systems which enable more accurate and reliable dosage administration to the patient, while simultaneously satisfying patient comfort requirements, all in a convenient device under the direct control of the patient, doctor, or therapist, and which also obviates the need for a high degree of skill or subjective expertise on the part of medical personnel or a patient attempting to reliably measure dosage. The present invention fulfills all these needs.

SUMMARY OF THE INVENTION

Briefly, and in general terms, the present invention provides a method and apparatus for electrical dosimetry control in the application of electric currents to a suitable load, such as the human body, dosage being determined by the product of time and administered electrical current, wherein electrical current magnitude and/or time may be selectively varied by the operator, patient, or therapist during an administration procedure, for the comfort or convenience of the patient, all without altering the total predetermined dosage to be administered. Hence, electrical current and/or time can be varied and still produce a consistently reliable total administered dose from one procedure to the next.

Basically, the present invention is directed to a system for electrical dosimetry measurement and control, wherein the product of administered electrical current and time for total dosage is maintained constant, while either variable, time or electrical current magnitude, may be changing.

Such a system, by way of example and not necessarily by way of limitation, may include means for applying electrical current to a load, such as a human patient, over time, together with means for selectively varying the magnitude of the current, as for patient comfort or convenience. In addition, the system includes means for establishing the magnitude of the desired total dosage in terms of delivered time-current product and means for sensing the magnitude of the electrical current and converting that magnitude to a voltage for varying the frequency of a voltage controlled oscillator as a function of the electrical current magnitude. Means are also provided for measuring and accumulating the electrical output of the oscillator over time, in a suitable counting device, as an indication of the actually delivered time-current product. In addition, means are provided for comparing the delivered time-current product registered in the counter, as a running measure of dosage during the administration procedure, with the desired total dosage previously established, so that the application of electrical current to the load will be terminated when the time-current product actually administered equals the desired total dosage.

In this way, desired dosage is consistently and reliably delivered, with great precision, even though the electrical current may be varied during the administration procedure for the convenience and comfort of the patient.

The new and improved electrical dosimetry control system of the present invention is extremely accurate, reliable and easy to use. The system provides enhanced patient comfort and high precision in establishing administered dosage whether it be in the form of medication infused by an iontophoretic device or electrical treatment current in galvanic therapy. Hence, the system of the present invention not only ensures greater patient comfort, but minimizes the time-consuming and error-prone aspects of manual techniques for measuring and controlling dosimetry, and obviates the need for a high degree of skill and subjective expertise on the part of medical personnel required to make such measurements.

These and other objects and advantages of the invention will become apparent from the following more detailed description, when taken in conjunction with the accompanying drawings of illustrative embodiments.

DESCRIPTION OF THE PREFERRED EMBODIMENT

Figure 1:
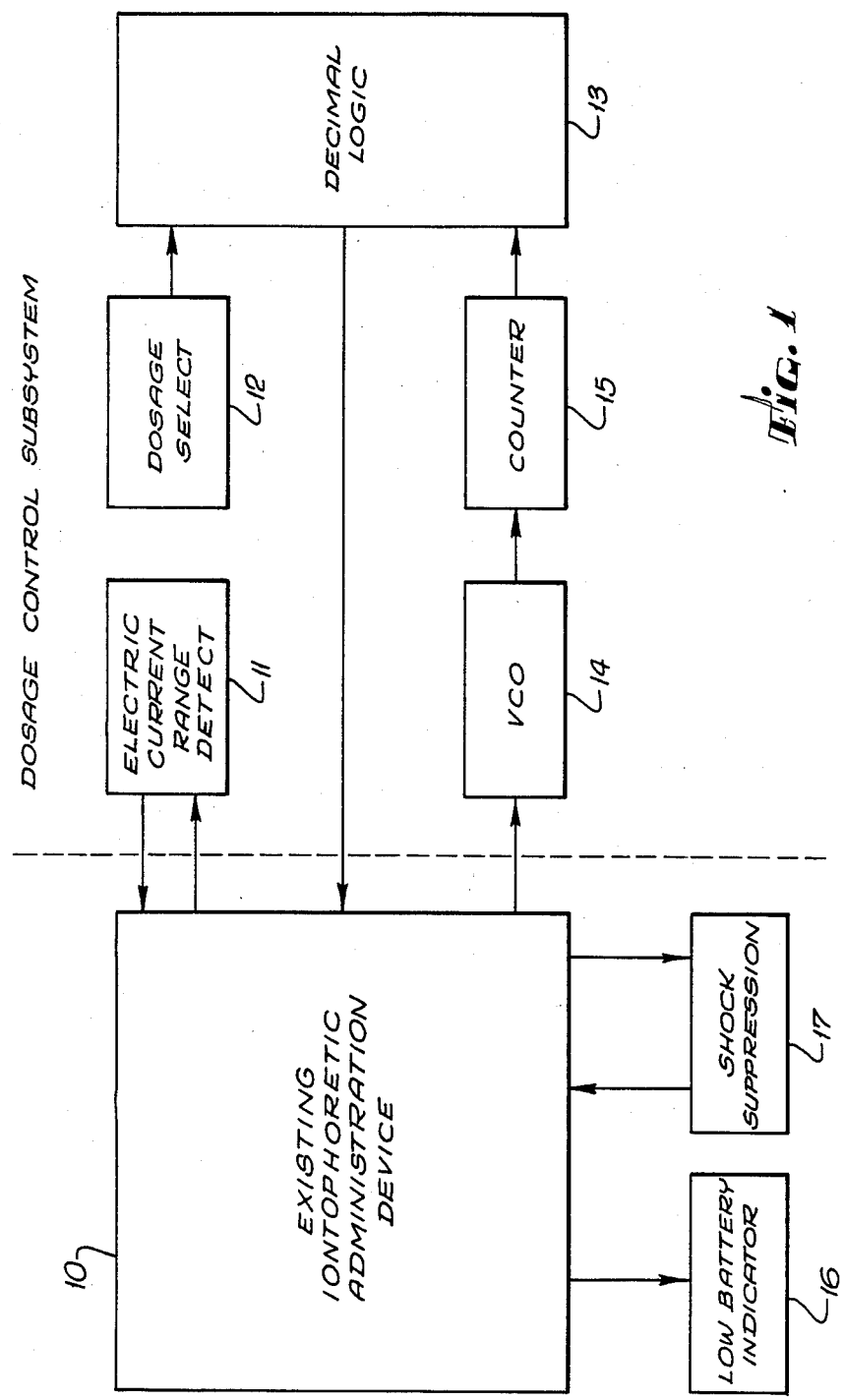
FIG. 1 is an overall block diagram of a generalized electrical dosimetry control system, interacting with an existing iontophoretic administration device, in accordance with the present invention.

Referring now to the drawings, and more particularly to FIG. 1, there is shown a system for electrical dosimetry control in the application of electrical currents to any suitable load, such as the human body, in accordance with the present invention. While the dosage measuring and control system of this invention can be used with or without medication, the devices generating the electrical output signal which the system is designed to control, can vary considerably in design. For example, iontophoresis and galvanic devices are generally recognized as units that generate and deliver a D.C. signal to be effective. In this regard, there can be considerable variation from a pure D.C. signal to a pulsating D.C. signal, and even to a momentary reversal of polarity, so long as there is a net delivery of electrical current in a single direction.

An existing iontophoretic administration device 10, or other suitable apparatus for applying electrical current, provides a variable output electrical current to any appropriate load (not shown), such as a human patient. Such an iontophoretic administration device 10 may be a "DRIONIC" iontophoresis device, manufactured and sold by General Medical Company, Los Angeles, Calif.

Electrical current magnitude is established and detected in the system of FIG. 1 by a combination of the iontophoretic device 10, a suitable electrical current range detection subsystem 11 and associated switching circuitry (not shown).

The desired total dosage to be administered to the load is selected by a dosage selection subsystem 12 and directed to an appropriate decimal logic unit 13, typically a digital storage register and comparator, or its equivalent.

The electrical load current of the iontophoretic device is sensed and converted to an appropriate voltage which is directed to a suitable voltage controlled oscillator (VCO) 14. The oscillator 14 generates output pulses whose frequency is proportional to the magnitude of the load current, and this electrical pulse output is directed to a counter 15 which essentially integrates the applied load current over time, via the counting of oscillator output pulses, to obtain an electrical current-time product providing a running measure of dosage actually delivered to the load during the administration procedure.

The state of the counter 15, i.e., the actually delivered dosage, is directed to the decimal logic unit 13 where it is compared with the selected total dosage desired and, when the running measure of dosage indicated by the counter matches the total dosage selected, the iontophoretic administration device 10 is disabled by an appropriate output from the decimal logic unit. In this way, any variations in current and/or time during the administration procedure will still provide a consistently reliable total dosage from one procedure to the next and, therefore, the parameters of time and electrical current can be varied at will to suit the comfort and convenience of the patient, without interfering with the precise total dosage administered to the patient over the course of the procedure.

Low battery indication and shock suppression subsystems 16, 17 respectively, are also provided as peripheral subsystems to the iontophoretic administration device 10 to further enhance its safety and effective operation.

Figure 2:
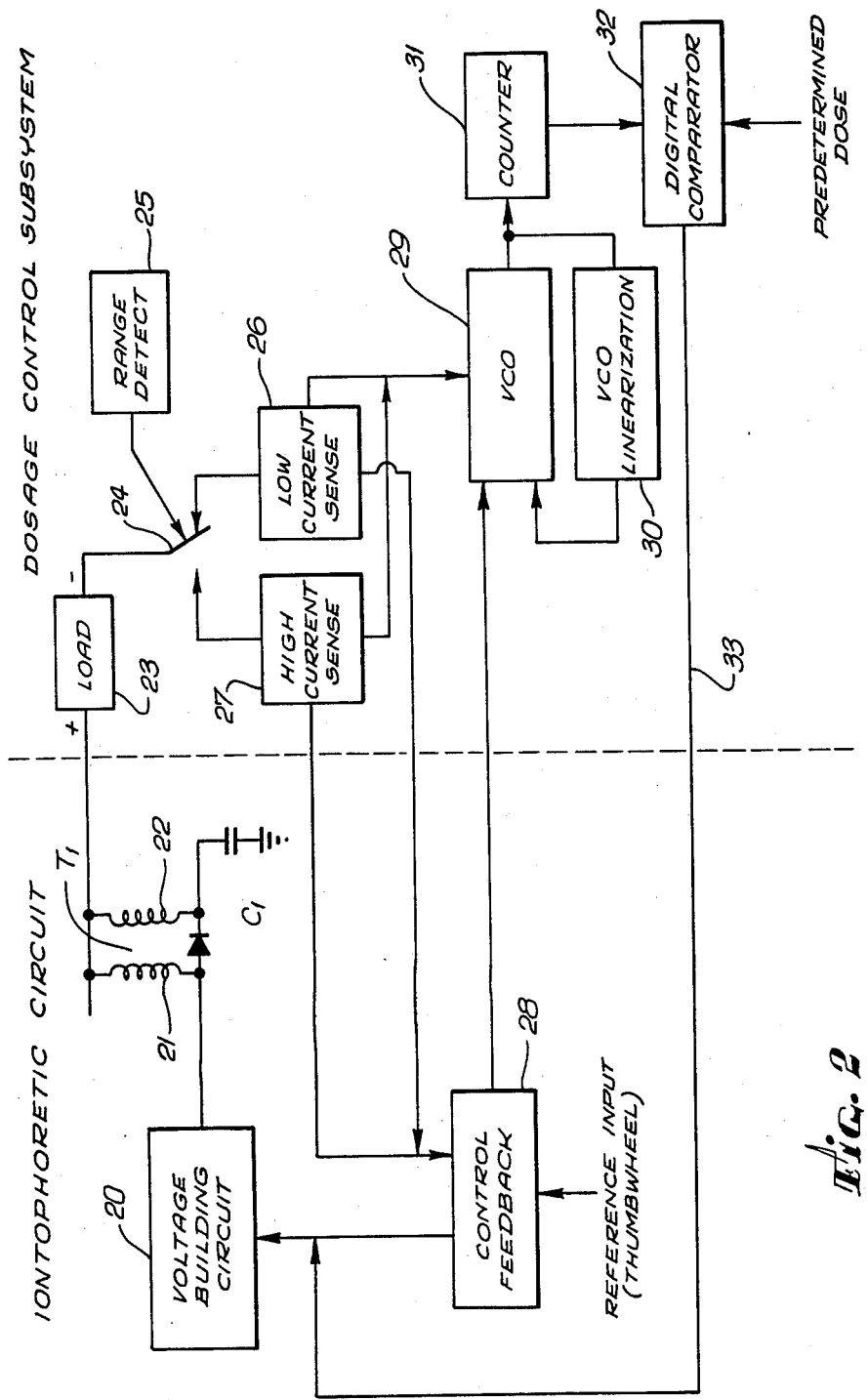
FIG. 2 is a combined block diagram and electrical schematic illustrating further details of the dosimetry control system of the invention.

Referring now more particularly to FIG. 2 of the drawings, there is shown a voltage building circuit 20, within any suitable iontophoretic device or the like, such as the previously mentioned "DRIONIC" iontophoretic device, whose electrical output is directed to a switching mode feedback regulator or the like. In this regard, an electrical voltage is built up on a capacitor C1 through inductive flyback action by the pumping of stored magnetic energy in the primary winding 21 of a transformer T1.

An electrical load 23, which typically is some part of the human anatomy, is connected to capacitor C1 through the secondary winding 22 of transformer T1. The load 23 receives the negative pulses that appear on the secondary winding 22 caused by the flyback action on the primary winding 21. The load voltage thus consists of the D.C. voltage on capacitor C1 with superimposed pulses from the secondary winding 22.

The load 23 is ungrounded, with its positive terminal connected to the secondary winding 22 of transformer T1, and its negative terminal connected through a suitable switching arrangement 24 to a range detection subsystem 25, and low current and high current sensing subsystems 26, 27, respectively. The low current and high current sensing subsystems 26, 27 interact with the iontophoretic circuit via a control feedback network 28 which, in turn, interacts with the voltage building circuit 20 to control its output and, therefore, set the load current. The feedback network 28 also directs an output to a voltage controlled oscillator 29 which also interacts with the high current and low current sensing subsystems 27, 26. A VCO linearization subsystem 30 is also provided to stabilize the electrical output of the oscillator 29.

A reference input is provided to the control feedback network 28 by means of a thumbwheel or the like (not shown) which enables the operator, such as a patient, therapist, or other medical personnel to alter the load current administered to the patient. Hence, the load current can be readily adjusted for patient comfort without affecting in any way the total dosage administered by the system. If current is lowered, time of administration will be increased, if current is increased, time will be decreased, all to the end that the total dosage to be administered will be constant.

The load current is converted to a voltage which establishes the frequency of oscillation of the oscillator 29. A counter 31 accumulates the electrical output of the oscillator 29 over time, as an indication of the actually delivered time-electrical current product representing a running measure of dosage during the administration procedure.

The electrical state of the counter 31 is then directed as input to a digital comparator 32 and, when the state of the counter 31 equals the desired total dosage to be administered, represented by a predetermined dose already set in the digital comparator, an electrical output is generated from the comparator. This output is directed, over line 33, to the iontophoretic circuit to terminate the administration procedure once the desired total dosage has been delivered to the patient. Consequently, the desired total dosage is consistently and reliably delivered to the patient, with great precision, from one administration procedure to the next. This precise repeatability occurs even though the electrical current may be varied substantially during the administration procedure for the convenience and comfort of the patient.

Hence, the new and improved method and apparatus for electrical dosimetry control, afforded by the present invention, provides a system which is extremely accurate, reliable and easy to use by the operator. The system provides very high precision in consistently and reliably establishing administered dosage whether it be in the form of medication infused by an iontophoretic device or electrical treatment current in galvanic therapy. In this way, the system of the present invention not only ensures greater patient comfort, but minimizes the time-consuming and error-prone aspects of manual techniques for measuring and controlling dosimetry, thus obviating the need for a high degree of skill and subjective expertise on the part of medical personnel often required to make such measurements. It will be apparent that the various subsystems indicated in FIGS. 1 and 2 of the drawings can be implemented readily by those of ordinary skill in the art without the exercise of inventive skill.

Accordingly, it will be apparent from the foregoing that, while particular forms of the invention have been illustrated and described, various modifications can be made without departing from the spirit and scope of the invention. Therefore, it is not intended that the invention be limited, except as by the appended claims.

I claim:

1. In an electronic control system for iontophoretic delivery of electrical current over time to a biological subject, the combination comprising:
   means for determining the magnitude of said electrical current delivered to the biological subject;
   means for controlling the time period over which electrical current is supplied to the biological subject;
   adjustable means for selecting the dosage to be delivered to the biological subject;
   means for electrically measuring the actual dosage applied to the biological subject as a function of the produce of said electrical current and time; and
   means for terminating said electrical current delivered to the biological subject when said electrical current-time product equals said desired total dosage to be administered as established by said adjustable means.

2. An electronic process for controlling iontophoretic delivery of electrical current over time to a biological subject, comprising the steps of:
   selecting a total dosage to be administered in the form of an electrical current-time product delivered to the biological subject;
   determining the magnitude of said electrical current supplied to the biological subject;
   measuring said electrical current supplied to the biological subject and automatically varying the time period over which said electrical current is administered to the biological subject by accumulating the electrical current-time product until termination at the selected total dosage to be administered, whereby the need for mathematical calculation during current delivery is eliminated.

3. In an electronic control system for iontophoretic delivery of electrical current over time to a biological subject, the combination comprising:
   means for applying a predetermined electrical current to a biological subject over time;
   adjustable means for establishing the magnitude of the desired total dosage to be administered to the biological subject, in terms of delivered electrical current-time product;
   means for sensing said magnitude of the electrical current delivered to the biological subject and for converting said magnitude of said electrical current to an electrical signal;
   oscillator means responsive to said electrical signal for varying the frequency of oscillation as a function of said magnitude of said electrical current;
   means for measuring and accumulating the electrical output of said oscillator over time as an indication of actually delivered electrical current-time product;
   means for comparing said actually delivered electrical current-time product with said desired total dosage to be administered; and
   means for terminating said electrical current delivered to the biological subject when said electrical current-time product equals said desired total dosage to be administered as established by said adjustable means.

4. A combination as set forth in claim 1 or 3, wherein the iontophoretic system delivers a therapeutic agent to the biological subject.

5. A combination as set forth in claim 1 or 3, wherein the iontophoretic system delivers a chemical agent to the biological subject.

* * * * *

UNITED STATES PATENT AND TRADEMARK OFFICE
CERTIFICATE OF CORRECTION

PATENT NO. : 4,822,334
DATED : April 18, 1989
INVENTOR(S) : Robert Tapper

It is certified that error appears in the above-identified patent and that said Letters Patent is hereby corrected as shown below:

Column 6, line 13, delete "produce" and insert therefor --product--.

Signed and Sealed this

Fourth Day of June, 1991

*Attest:*

HARRY F. MANBECK, JR.

*Attesting Officer*       *Commissioner of Patents and Trademarks*